United States Patent

Williams et al.

Patent Number: 5,373,023
Date of Patent: Dec. 13, 1994

[54] TETRAHYDRONAPHTALENE DERIVATIVES, THEIR PREPARATION AND PHARMACEUTICAL COMPOSITIONS CONTAINING THEM

[75] Inventors: Paul Howard Williams; Christian Hoornaert, both of Paris; Jean Claude Muller, Morsang s/Orge, all of France

[73] Assignee: SYNTHELABO, Le Plessis Robinson, France

[21] Appl. No.: 101,764

[22] Filed: Aug. 4, 1993

[30] Foreign Application Priority Data

Aug. 5, 1992 [FR] France .................. 92 09713

[51] Int. Cl.⁵ .............. A61K 31/165; C07C 233/65; C07C 55/07; C07C 53/06
[52] U.S. Cl. .................. 514/617; 514/352; 514/357; 514/452; 514/456; 514/522; 514/563; 514/574; 514/613; 546/309; 546/335; 549/366; 558/411; 562/595; 562/597; 562/609; 564/180; 564/161
[58] Field of Search ............... 564/180; 514/617, 613, 514/574, 563; 562/595, 597, 609

[56] References Cited

U.S. PATENT DOCUMENTS

| | | | |
|---|---|---|---|
| 3,366,674 | 1/1968 | Geiger | 260/501.17 |
| 5,001,159 | 3/1991 | Hoornaert et al. | 514/619 |
| 5,066,680 | 11/1991 | Shiokawa et al. | 564/39 |
| 5,137,901 | 8/1992 | Junge et al. | 514/373 |

FOREIGN PATENT DOCUMENTS 0233762 8/1987 European Pat. Off.
0352613 1/1990 European Pat. Off.

*Primary Examiner*—Shailendra Kumar
*Attorney, Agent, or Firm*—Jacobson, Price, Holman & Stern

[57] ABSTRACT

The invention provides compounds which are tetrahydronaphthalene derivatives of the formula (I)

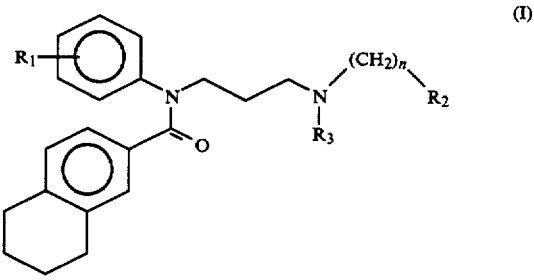

wherein $R_1$ represents a halogen atom, a cyano group, a nitro group, an unbranched ($C_1$-$C_6$) alkoxy group, a ($C_1$-$C_6$ cycloalkyl) ($C_1$-$C_2$ alkoxy) group or an aryl ($C_1$-$C_2$ alkoxy) group, $R_2$ represents a ($C_1$-$C_4$) alkyl group, an aryl group optionally substituted with at least one methoxy group, a pyridyl group or a benzodioxanyl group, $R_3$ represents a hydrogen atom or a ($C_1$-$C_2$) alkyl group, and n=0 to 3, or are addition salts with pharmaceutically acceptable acids. The compounds of the invention have anti-ischaemic activity.

6 Claims, No Drawings

TETRAHYDRONAPHTALENE DERIVATIVES, THEIR PREPARATION AND PHARMACEUTICAL COMPOSITIONS CONTAINING THEM

The present invention relates to tetrahydronaphthalene derivatives and acid addition salts thereof, to their preparation and to pharmaceutical compositions containing them.

According to the invention there is provided a compound which is a tetrahydronaphthalene derivative of the formula (I)

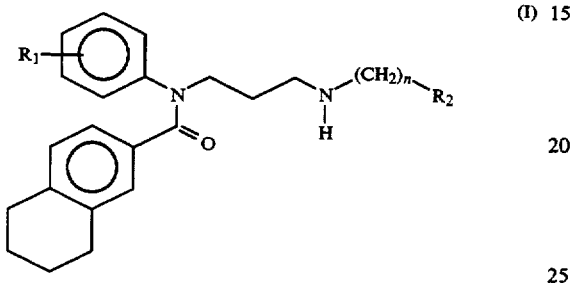

wherein
- $R_1$ represents a halogen atom, a cyano group, a nitro group, an unbranched or branched ($C_1$–$C_6$) alkoxy group, a ($C_1$–$C_6$ cycloalkyl) ($C_1$–$C_2$ alkoxy) group or an aryl ($C_1$–$C_2$ alkoxy) group,
- $R_2$ represents a ($C_1$–$C_4$) alkyl group, an aryl group optionally substituted with at least one methoxy group, a pyridyl group or a benzodioxanyl group,
- $R_3$ represents a hydrogen atom or a ($C_1$–$C_2$) alkyl group, and n=0 to 3, or is an addition salt with a pharmaceutically acceptable acid.

Preferred compounds of the invention are those wherein $R_1$ represents an unbranched or branched ($C_1$–$C_6$) alkoxy group, $R_2$ represents an aryl group substituted with at least one methoxy group, $R_3$ represents a ($C_1$–$C_2$) alkyl group, and n=2.

Among these preferred compounds, the compound of choice is the compound corresponding of formula (I) in which $R_1$ represents a 2-methylpropoxy group, $R_2$ represents a 3,4-dimethoxyphenyl group, $R_3$ represents a methyl group and n=2.

Other preferred compounds of the invention are those wherein $R_1$ represents a fluorine atom, a cyano group, a nitro group, —$OCH_3$, —$OCH_2CH(CH_3)_2$ or —$OCH_2C_6H_{11}$, $R_2$ represents phenyl optionally substituted with at last one methoxy group, pyridyl, methyl or benzodioxanyl and $R_3$ represents hydrogen, methyl or ethyl. Particularly preferred compounds are N-[3-[[2-(3,4-dimethoxyphenyl)ethyl]methylamino]-propyl]-N-[2-(2-methylpropoxy)phenyl]-5,6,7,8-tetrahydronaphthalene-2-carboxamide or its oxalate and N-[2-(2-methylpropoxy)phenyl]-N-[3-[(2-phenylethyl)amino]propyl-5,6,7,8-tetrahydronaphthalene-2-carboxamide or its fumarate.

The compounds of the invention can take the form of the free bases of formula (I) or their addition salts with pharmaceutically acceptable acids.

The compounds of the invention in which $R_3$ represents a hydrogen atom may be prepared according to Scheme 1 below:

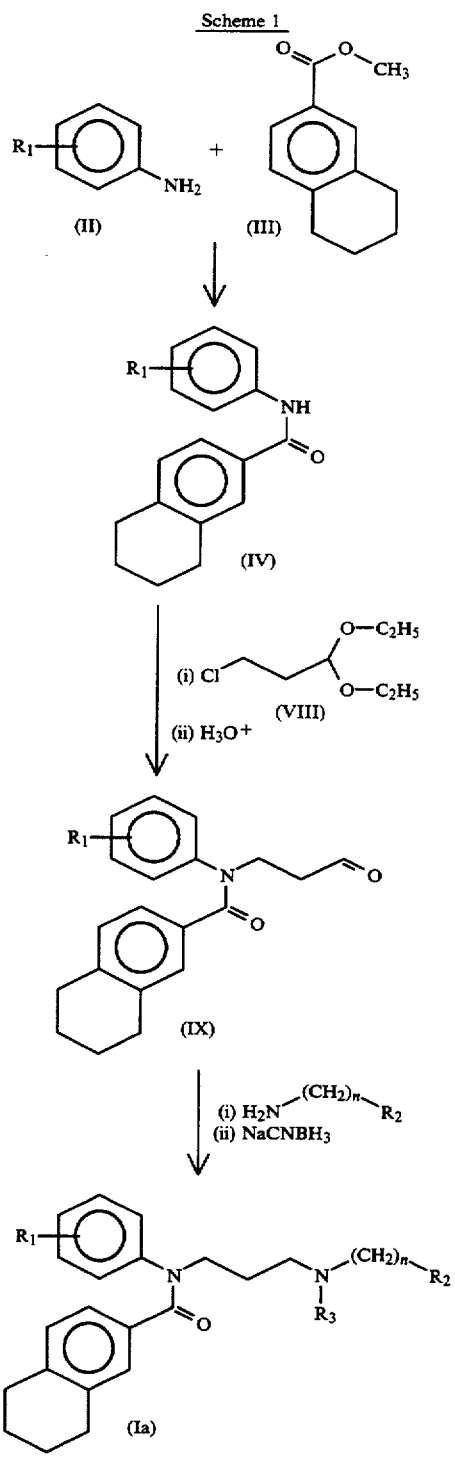

In accordance with Scheme 1 methyl 5,6,7,8-tetrahydronaphthalene-2-carboxylate (III) is reacted with an amine of formula (II), in which $R_1$ is as defined above, to obtain a carboxamide of formula (IV), which is condensed with 3-chloro-1,1-diethoxypropane of formula (VIII) to obtain a carboxamide, which is treated in an acid medium to give a carboxamide of formula (IX), which compound is condensed with an amine of formula (X), in which $R_2$ and n are as defined above, suitably in the presence of sodium cyanoborohydride, in a solvent such as methanol, to obtain a carboxamide of formula (I a).

According to the invention, the compounds of general formula (I) in which $R_3$ represents a $(C_1-C_2)$ alkyl group may be prepared according to Scheme 2 below:

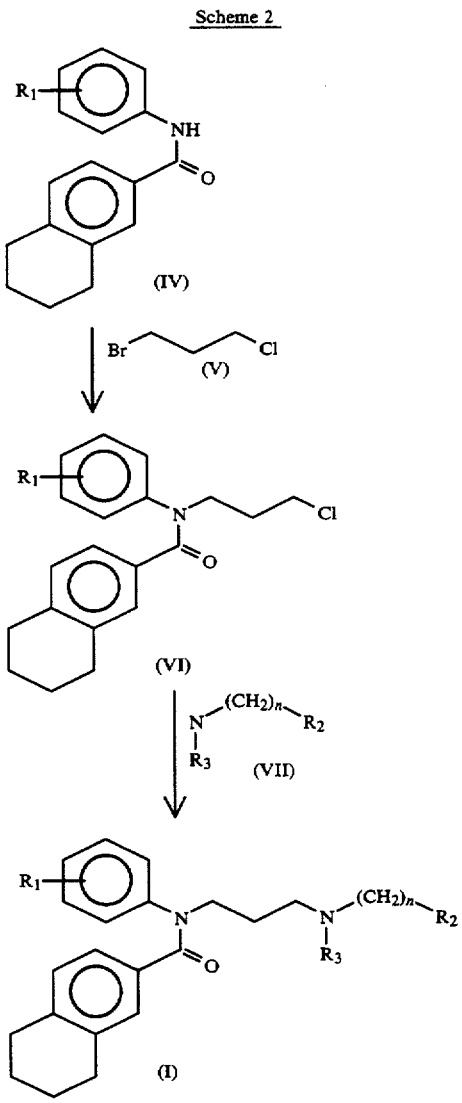

In accordance with Scheme 2 the compound of formula (IV) is condensed with 1-bromo-3-chloropropane of formula (V), in the presence of a base such as sodium hydride, to obtain a compound of formula (VI) which is reacted with an amine of formula (VII), in which $R_2$, $R_3$ and n are as defined above, to obtain the compound of general formula (I). If desired the compounds of formula (Ia) or (I) prepared in accordance with Schemes 1 and 2 can be converted, in manner known per se, to their acid addition salts.

Methyl 5,6,7,8-tetrahydronaphthalene-2-carboxylate (III) is prepared from 5,6,7,8-tetrahydro-2-naphthol, which is reacted with trifluoromethanesulphonic anhydride to obtain 5,6,7,8-tetrahydro-2-naphthyl trifluoromethanesulphonate, which is converted to the carboxylate of formula (III).

The benzenamine of formula (II) may be prepared by various methods known to a person skilled in the art.

The other starting materials are commercially available.

Certain intermediate compounds are new and also form part of the invention. They correspond to the formula (XI)

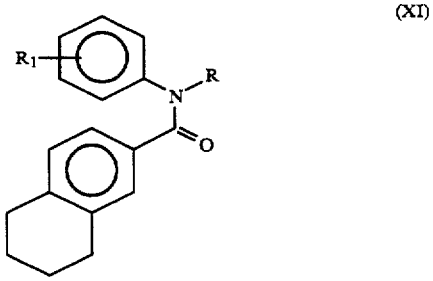

in which R represents a hydrogen atom, a 3-chloropropyl group or a 3-oxopropyl group and $R_1$ is as defined above.

The Examples which follow illustrate in detail the preparation of a few compounds according to the invention. The structures of the products obtained were confirmed by elemental microanalyses and IR and NMR spectra.

EXAMPLE 1

N-[3-[[2-(3,4-Dimethoxyphenyl)ethyl]methylamino]-propyl]-N-[2-(2-methylpropoxy)phenyl]-5,6,7,8-tetrahydronaphthalene-2-carboxamide oxalate

1.1 1-(2-methylpropoxy)-4-nitrobenzene 98.66 g (0.72 mol) of 1-bromo-2-methylpropane, 74.63 g (0.54 mol) of potassium carbonate and 250 ml of dimethylformamide are added to 50 g (0.36 mol) of 4-nitrophenol. The mixture is heated to 100° C. for 4 hours and then evaporated to dryness. The residue is taken up with 500 ml of 1N sodium hydroxide solution, and 200 ml of ether are added. The organic phase is recovered and washed successively three times with 100 ml of 1N sodium hydroxide, then three times with 200 ml of water and finally with 100 ml of saturated sodium chloride solution. It is dried over magnesium sulphate and evaporated to dryness.

70 g of product are obtained.

1.2 4-(2-methylpropoxy)benzenamine 22 g (0.11 mol) of the compound obtained in 1.1, 200 ml of ethanol and some platinum oxide are added into a Parr apparatus. A catalytic hydrogenation is carried out for 3 hours at room temperature at a pressure of 0.28 MPa. The mixture is filtered through Celite and the Celite is washed with ethanol. The filtrate is evaporated to dryness and 18 g of product are obtained, which product is purified by distillation. 33.5 g of pure product are obtained. Boiling point=86°-92° C. at a pressure of 200 Pa.

1.3 5,6,7,8-tetrahydro-2-naphthyl trifluoromethanesulphonate 17.5 g (0.12 mol) of 5,6,7,8-tetrahydro-2-naphthol, 28.86 g (0.24 mol) of 4-dimethylaminopyridine, 20.64 ml (0.18 mol) of 2,6-dimethylpyridine and 400 ml of dichloromethane are placed in a 1-liter round-bottomed flask. The mixture is cooled to −30° C. under argon. 50 g (0.18 mol) of trifluoromethanesulphonic anhydride in 120 ml of dichloromethane are added dropwise, and the mixture is then allowed to return to room temperature. 500 ml of dichloromethane are then added and the organic phase is washed successively with 200 ml of 1N hydrochloric acid, three times 200 ml of water, 200 ml of saturated sodium hydrogen carbonate solution, twice 200 ml of water and 200 ml of saturated sodium chloride solution. It is dried over sodium sulphate and evaporated to dryness. The residue is purified by chromatography on a column of silica gel, eluting with hexane.

1.4 methyl 5,6,7,8-tetrahydronaphthalene-2-carboxylate

In a 1-liter three-necked round-bottomed flask, 32.3 g (0.12 mol) of the compound obtained in 1.3 are solubilised in 345 ml of dimethyl sulphoxide and 230 ml of methanol. 35.21 ml (0.35 mol) of triethylamine, 0.8 g (0.004 mol) of palladium acetate and 1.44 g (0.004 mol) of 1,3-bis(diphenylphosphino)propane are added. A stream of carbon monoxide is bubbled through the mixture for 5 minutes, and the latter is then heated to 70° C. under a carbon monoxide atmosphere for 4 hours. 400 ml of water are then added and the mixture is extracted twice with 200 ml of ether. The ether phases are washed with 200 ml of water, dried over magnesium sulphate and evaporated to dryness. The residue is purified by chromatography on a column of silica gel, eluting with a dichloromethane/hexane (4:6) mixture.

1.5
N-[2-(2-Methylpropoxy)phenyl]-5,6,7,8-tetrahydronaphthalene-2-carboxamide 1.3 g of a 50% suspension in oil of sodium hydride (0.033 mol) are placed in 10 ml of dimethyl sulphoxide containing one drop of methanol, under argon and with magnetic stirring. The mixture is left stirring for 10 minutes and 2.6 g (0.016 mol) of 4-(2-methylpropoxy)-benzenamine obtained in 1.2 are added. The mixture is left stirring for a few minutes and 2.5 g (0.013 mol) of the compound obtained in 1.4, dissolved in 10 ml of dimethyl sulphoxide, are then added dropwise. The mixture is left stirring for 4 hours at room temperature. 200 ml of water, 100 ml of ether and 100 ml of ethyl acetate are then added successively. The organic phase is separated and washed successively with 100 ml of water, 100 ml of 1N hydrochloric acid, twice 50 ml of water and 100 ml of sodium chloride. It is dried over magnesium sulphate and evaporated to dryness.

1.6
N-(3-chloropropyl)-N-[2-(2-methylpropoxy)phenyl]-5,6,7,8-tetrahydronaphthalene-2-carboxamide 2.58 g (0.008 mol) of the compound obtained above in 1.5, dissolved in 13 ml of dimethylformamide, are added into a round-bottomed flask with stirring and under nitrogen. 0.5 g of a 50% suspension in oil of sodium hydride (0.01 mol) is added slowly, the mixture is cooled to 0° C. and 1.88 g (0.01 mol) of 1-bromo-3-chloropropane are added dropwise. The temperature is allowed to rise to room temperature and the mixture is left stirring for 4 hours. The solution is cooled and 100 ml of water and 100 ml of ether are added. The mixture is stirred, the organic phase is recovered and the aqueous phase is extracted with 100 ml of ether. The organic phases are combined and washed successively with twice 50 ml of water, 50 ml of 1N hydrochloric acid, twice 50 ml of water and 50 ml of saturated sodium chloride solution. They are dried over magnesium sulphate and evaporated to dryness.

3.3 g of product are obtained.

1.7
N-[3-[[2-(3,4-dimethoxyphenyl)ethyl]methylamino]-propyl]-N-[2-(2-methylpropoxy)phenyl]-5,6,7,8-tetrahydronaphthalene-2-carboxamide oxalate A mixture of 2 g (0.006 mol) of the compound obtained above in 1.6, 1.54 g (0.01 mol) of potassium carbonate, 0.93 g (0.006 mol) of potassium iodide and 1.1 g (0.006 mol) of 3,4-dimethoxy-N-methylbenzene-ethanamine is heated to 80° C. for 5 hours. The solution is cooled and 100 ml of water and 100 ml of ether are added. The organic phase is recovered and the aqueous phase is re-extracted with 100 ml of ether. The organic phases are combined and washed with three times 100 ml of water. They are dried over magnesium sulphate and evaporated to dryness. The residue is purified by chromatography on a column of silica gel, eluting with a dichloromethane/methanol (9:1) mixture. 0.7 g of product is obtained.

The oxalate is prepared by adding one equivalent of oxalic acid.

Melting point=114°–116° C.

EXAMPLE 2

N-[2-(2-Methylpropoxy)phenyl)-N-[3-[(2-phenylethyl)amino]propyl-5,6,7,8-tetrahydronaphthalene-2-carboxamide fumarate 2.1
N-(3,3-diethoxypropyl)-N-[2-(2-methylpropoxy)-phenyl]-5,6,7,8-tetrahydronapahthalene-2-carboxamide 9.7 g (0.03 mol) of the compound obtained in 1.5, dissolved in 25 ml of dimethylformamide, are added under nitrogen to 1.6 g of a 50% suspension in oil of sodium hydride (0.03 mol) in 20 ml of dimethyl sulphoxide. The mixture is heated to 50° C. for 1 hour 30 minutes and 5.5 g (0.03 mol) of 3-chloro-1,1-diethoxypropane are added. The mixture is heated to 100° C. in an oil bath for 8 hours. It is then poured into an ice+water mixture and the product is extracted with ether. The organic phase is washed with water and then with saturated sodium chloride solution. It is dried over magnesium sulphate and the residual oil is purified by chromatography on a column of silica gel, eluting with a hexane/ethyl acetate (4:1) mixture.

4.3 g of product are obtained.

2.2
N-[2-(2-methylpropoxy)phenyl]-N-(3-oxopropyl)-5,6,7,8-tetrahydronaphthalene-2-carboxamide 4.3 g (0.009 mol) of the compound obtained above in 2.1, in 100 ml of hydrochloric acid, are heated to 50° C. for 4 hours in an oil bath. The reaction medium is then neutralised with sodium hydrogen carbonate and extracted with ether. The organic phase is recovered and washed with saturated sodium chloride solution. It is dried over magnesium sulphate and evaporated to dryness. The residue is purified by chromatography on a column of silica gel, eluting with an ethyl acetate/hexane (2:3) mixture.

2.7 g of product are obtained.

2.3 N-[2-(2-methylpropoxy)phenyl]-N-[3-[(2-phenylethyl)amino]propyl]-5,6,7,8-tetrahydronaphthalene-2-carboxamide fumarate 0.25 g of 3Å sieve, then 1.5 g (0.013 mol) of benzeneethanamine, then 0.625 ml of 6N hydrochloric acid and 0.12 g (0.002 mol) of sodium cyanoborohydride are added to a solution of 0.947 g (0.003 mol) of the compound obtained above in 2.2, in 25 ml of methanol, under nitrogen. The mixture is left at room temperature overnight. 1 ml of ethanolic hydrogen chloride and 0.4 g of sodium cyanoborohydride are then added and the mixture is left stirring for 3 hours. More ethanolic hydrogen chloride is added, the mixture is evaporated to dryness and the residue is taken up with water. The medium is neutralised with sodium carbonate and extracted with an ether/ethyl acetate mixture. The organic phase is recovered, washed with water, dried over magnesium sulphate and evaporated to dryness.

0.85 g of product is obtained.

The fumarate is prepared by adding one equivalent of fumaric acid and recrystallising in isopropyl alcohol.

Melting point = 148°–150° C.

The following table illustrates the chemical structures and the physical properties of a few compounds according to the invention.

TABLE

| No. | $R_1$ | $R_2$ | $R_3$ | n | Salt | M.p. (°C.) |
|---|---|---|---|---|---|---|
| 1 | 4-F | phenyl | —$CH_3$ | 2 | $C_2H_2O_4$ | 168–170 |
| 2 | 4-F | pyridin-2-yl | —$CH_3$ | 2 | 2 $C_2H_2O_4$ | 105–107 |
| 3 | 4-CN | phenyl | —$CH_3$ | 2 | $C_2H_2O_4$ | 209–211 |
| 4 | 4-CN | 2,3-dimethoxyphenyl ($OCH_3$, $OCH_3$) | —$CH_3$ | 2 | $C_2H_2O_4$ | 172–174 |
| 5 | 4-CN | pyridin-2-yl | —$CH_3$ | 2 | 2 HCl | 195–197 |
| 6 | 4-$NO_2$ | 2,3-dimethoxyphenyl ($OCH_3$, $OCH_3$) | —$CH_3$ | 2 | $C_2H_2O_4$ | 171–173 |
| 7 | 4-$OCH_3$ | phenyl | —$CH_3$ | 2 | $C_2H_2O_4$ | 134–136 |
| 8 | 4-$OCH_3$ | 2,3-dimethoxyphenyl ($OCH_3$, $OCH_3$) | —$CH_3$ | 2 | $C_2H_2O_4$ | 112–113 |

TABLE-continued

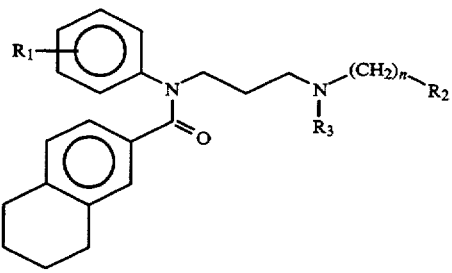

| No. | R₁ | R₂ | R₃ | n | Salt | M.p. (°C.) |
|---|---|---|---|---|---|---|
| 9 | 4-OCH$_3$ | 2-pyridyl | —CH$_3$ | 2 | 2 HCl | 185–187 |
| 10 | 4-OCH$_2$CH(CH$_3$)$_2$ | —CH$_3$ | —CH$_3$ | 0 | C$_2$H$_2$O$_4$ | 142–144 |
| 11 | 4-OCH$_2$CH(CH$_3$)$_2$ | phenyl | —CH$_3$ | 2 | C$_4$H$_4$O$_4$ | 138–140 |
| 12 | 4-OCH$_2$CH(CH$_3$)$_2$ | 3,4-dimethoxyphenyl | —CH$_3$ | 2 | C$_2$H$_2$O$_4$ | 114–116 |
| 13 | 4-OCH$_2$CH(CH$_3$)$_2$ | 3,4,5-trimethoxyphenyl | —CH$_3$ | 2 | C$_4$H$_4$O$_4$ | 118–120 |
| 14 | 4-OCH$_2$CH(CH$_3$)$_2$ | 2-pyridyl | —CH$_3$ | 2 | 2C$_2$H$_2$O$_4$ | 138–140 |
| 15 | 4-OCH$_2$CH(CH$_3$)$_2$ | 4-pyridyl | —CH$_3$ | 2 | 2 C$_2$H$_2$O$_4$ | 171–173 |
| 16 | 4-OCH$_2$CH(CH$_3$)$_2$ | 4-pyridyl | —CH$_3$ | 1 | 2 HCl | 154–156 |
| 17 | 4-OCH$_2$CH(CH$_3$)$_2$ | 1,4-benzodioxan-6-yl | —CH$_3$ | 1 | C$_4$H$_4$O$_4$ | 82–84 |
| 18 | 2-OCH$_2$CH(CH$_3$)$_2$ | —CH$_3$ | —CH$_3$ | 3 | C$_2$H$_2$O$_4$ | 148–150 |
| 19 | 2-OCH$_2$CH(CH$_3$)$_2$ | phenyl | —H | 2 | C$_4$H$_4$O$_4$ | 148–150 |
| 20 | 2-OCH$_2$CH(CH$_3$)$_2$ | phenyl | —CH$_3$ | 2 | C$_2$H$_2$O$_4$ | 173–175 |

TABLE-continued

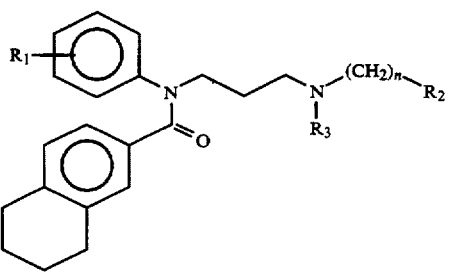

| No. | R₁ | R₂ | R₃ | n | Salt | M.p. (°C.) |
|---|---|---|---|---|---|---|
| 21 | 2-OCH$_2$CH(CH$_3$)$_2$ | 3,4-dimethoxyphenyl | —CH$_3$ | 2 | C$_2$H$_2$O$_4$ | 115–120 |
| 22 | 2-OCH$_2$CH(CH$_3$)$_2$ | 2-pyridyl | —CH$_3$ | 2 | / | oil |
| 23 | 2-O(CH$_2$)$_2$CH(CH$_3$)$_2$ | phenyl | —CH$_3$ | 2 | C$_2$H$_2$O$_4$ | 144–146 |
| 24 | 4-OCH$_2$C$_6$H$_{11}$ | phenyl | —CH$_3$ | 2 | C$_2$H$_2$O$_4$ | 122–124 |
| 25 | 4-OCH$_2$C$_6$H$_{11}$ | 3,4-dimethoxyphenyl | —CH$_3$ | 2 | C$_2$H$_2$O$_4$ | 116–118 |
| 26 | 4-OCH$_2$C$_6$H$_{11}$ | 2-pyridyl | —CH$_3$ | 2 | 2 HCl | 164–166 |
| 27 | 4-OCH$_2$C$_6$H$_5$ | phenyl | —CH$_3$ | 2 | C$_2$H$_2$O$_4$ | 123–125 |

Legend:
in the "R$_1$" column, C$_6$H$_5$ denotes a phenyl group and C$_6$H$_{11}$ denotes a cyclohexyl group
in the "Salt" column, 2 HCl denotes a dihydrochloride, C$_2$H$_2$O$_4$ denotes an oxalate, 2 C$_2$H$_2$O$_4$ denotes a dioxalate and C$_4$H$_4$O$_4$ denotes a fumarate.

The compounds of the invention were subjected to pharmacological tests which showed their value as active substances in therapy.

Inhibition of KCl-Induced Calcium Entry in Sections of Immature Rat Cortex 8-day-old male or female Sprague-Dawley rats are used. After cervical dislocation, the brain is excised and sections of parietal cortex are prepared.

The intracellular calcium concentration ($[Ca^{2+}]_i$) is measured according to the technique described in J. Pharm. Exp. Ther., 261, (1992), page 324–330. The sections thus sampled are incubated for 75 minutes at 24° C. in Krebs buffer saturated with O$_2$/CO$_2$ (95%/5%) and containing Fura —2/AM at a concentration of 7 μM. After incubation, the sections are rinsed several times with this same buffer and left in this buffer until used. To measure the $[Ca^{2+}]_i$, the sections are placed at 30° C. in the cell of a spectrofluorimeter which is perfused with Krebs buffer by means of a pump. Depolarisation of the sections is carried out by perfusing Krebs buffer containing 50 mM KCl for 3 minutes. The test compound is introduced into the perfusion liquid 7 minutes after this first depolarisation, and a second depolarisation is carried out 7 minutes after the introduction of the test compound. The fluorescence is monitored at two excitation wavelengths, 340 nm (form bound to calcium) and 380 nm (free form), the emission wavelength being 510 nm. The $[Ca^{2+}]_i$ is calculated according to the method described in J. Biol. Chem., 260, (1985), 3440–3450. The inhibitory effect of the test compounds is calculated relative to the increase in [Ca$^{2+}$]$_i$ induced by 50 mM KCl, taken as 100%.

The percentage inhibition of Ca$^{2+}$ entry induced by the compounds of the invention is dose-dependent, and lies between 10 and 50%.

Occlusion of the Middle Cerebral Artery in Mice

The neuroprotective activity of the compounds of the invention was shown in a model of focal ischaemia by ligation of the middle cerebral artery in mice, according to a method similar to that described in Brain Research, 522, (1990), 290–307.

Six days after occlusion of the middle cerebral artery by electrocoagulation under halothane anaesthesia, the mice are anaesthetised again, and the cerebral cortex ipsilateral to the occlusion is removed. After homogenisation of the tissue, the extent of cerebral infarction is evaluated by measuring the increase in density of the peripheral benzodiazepine sites ($\omega_3$) using the New England Nuclear compound [$^3$H]-PK 11195. The treatments are administered curatively at times 5 minutes, 3 hours, 6 hours, 18 hours and 24 hours after the occlusion via the intraperitoneal route. The compounds of the invention decrease the density of the peripheral benzodiazepine sites by approximately 40% at a dose of 10 mg/kg.

The results of the tests show that the anti-ischaemic activity of the compounds of the invention is linked to their inhibitory effect on the calcium channels of the nervous tissue. They may hence be used in the prophylaxis or treatment of certain neuropathological states such as, in particular, cerebral ischaemia, epilepsy, cerebral ageing and neurodegenerative diseases.

To this end, they may be presented in all pharmaceutical dosage forms suited to enteral or parenteral administration, in combination with suitable excipients, for example in the form of tablets, dragées, capsules including hard gelatin capsules, suppositories or solutions or suspensions for oral use or for injection, containing doses to permit a daily administration of 5 to 500 mg of active substance.

We claim:

1. A compound which is a tetrahydronaphthalene derivative of the formula (I)

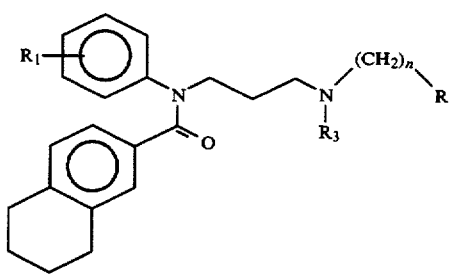

wherein

R$_1$ represents an atom or group selected from a halogen atom, a nitro group, an unbranched or branched (C$_1$–C$_6$) alkoxy group, a (C$_1$–C$_6$ cycloalkyl) (C$_1$–C$_2$ alkoxy) group and an aryl (C$_1$–C$_2$ alkoxy) group, R$_2$ represents a group selected from a (C$_1$–C$_4$) alkyl group, an aryl group optionally substituted with at least one methoxy group, R$_3$ represents an atom or group selected from a hydrogen atom and a (C$_1$–C$_2$) alkyl group, and n=0 to 3, or is an addition salt with a pharmaceutically acceptable acid.

2. A compound according to claim 1 wherein R$_1$ represents a (C$_1$–C$_6$) alkoxy group, R$_2$ represents an aryl group substituted with at least one methoxy group, R$_3$ is selected from methyl and ethyl and n=2.

3. A compound according to claim 1 wherein R$_1$ represents an atom or group selected from a fluorine atom, a nitro group, —OCH$_3$, —OCH$_2$CH(CH$_3$)$_2$ and —OCH$_2$C$_6$H$_{11}$, R$_2$ represents a group selected from phenyl optionally substituted with at last one methoxy group, and methyl and R$_3$ represents an atom or group selected from hydrogen, methyl and ethyl.

4. N-[3-[[2-(3,4-Dimethoxyphenyl(ethyl)methylamino]propyl]-N-[2-(2-methylpropoxy)phenyl]-5,6,7,8-tetrahydronaphthalene-2-carboxamide or its oxalate.

5. N-[2-(2-Methylpropoxy)phenyl]-N-[3-[(2-phenylethyl)amino]propyl-5,6,7,8-tetrahydronaphthalene-2-carboxamide or its fumarate.

6. A pharmaceutical composition which contains a compound as claimed in claim 1 in combination with a pharmaceutically acceptable excipient.

* * * * *